United States Patent [19]
Smits

[11] Patent Number: 5,336,269
[45] Date of Patent: Aug. 9, 1994

[54] METHOD AND APPARATUS FOR SWITCHING DEGREES OF FREEDOM IN A PROSTHETIC LIMB

[75] Inventor: Matthijs P. Smits, Brookline, Mass.
[73] Assignee: Liberty Mutual Insurance Co., Boston, Mass.
[21] Appl. No.: 896,058
[22] Filed: Jun. 9, 1992
[51] Int. Cl.⁵ .............................................. A61F 2/72
[52] U.S. Cl. ........................................ 623/25; 623/24
[58] Field of Search .................... 623/25, 57, 64, 24; 128/733

[56] References Cited

U.S. PATENT DOCUMENTS

| | | |
|---|---|---|
| 4,030,141 | 6/1977 | Graupe . |
| 4,087,730 | 5/1978 | Goles ................................. 318/603 |
| 4,209,860 | 7/1980 | Graupe . |
| 4,314,379 | 2/1982 | Tanie et al. ........................... 623/25 |

FOREIGN PATENT DOCUMENTS

| | | |
|---|---|---|
| 2509603 | 1/1983 | France ................................. 623/25 |
| 1604140 | 12/1981 | United Kingdom . |
| 2136617A | 9/1984 | United Kingdom . |

OTHER PUBLICATIONS

Development of the Utah Artificial Arm, IEEE vol. BME-29, No. 4 Apr. 1982, Jacobsen, Knutt, Johnson and Sears, pp. 249-269.

Primary Examiner—Randall L. Green
Assistant Examiner—D. Willse
Attorney, Agent, or Firm—Wolf, Greenfield & Sacks

[57] ABSTRACT

The invention comprises a method and apparatus for switching between degrees of freedom in a prosthesis responsive to myoelectric signals generated by muscles. In the invention, an average pattern corresponding to a specified muscle contraction is stored in memory. In operation, the invention continuously stores a specified preceding interval of the incoming myoelectric signals and compares the data in that interval with the stored average pattern. If the incoming data is sufficiently similar to the stored average pattern, a recognition occurs and the device switches degrees of freedom.

26 Claims, 3 Drawing Sheets

METHOD AND APPARATUS FOR SWITCHING DEGREES OF FREEDOM IN A PROSTHETIC LIMB

FIELD OF THE INVENTION

The invention pertains to controllers for prosthetic limbs. More particularly, the invention pertains to a method and apparatus for switching between degrees of freedom of a prosthetic limb.

BACKGROUND OF THE INVENTION

It is believed to be of great importance in the design of prosthetic limbs and their controllers that the limbs look and operate as much like actual human limbs as possible. Generally, amputees are disinclined to use prosthetic devices that appear unnatural in look or operation or which require unnatural movements to operate. Prosthetic limbs, such as the Liberty Mutual Boston elbow system, are able to provide limited functions for amputees corresponding to the functions of the original limb.

The operation of some prosthetic limbs is controlled, at least partially, by myoelectric signals of remnant muscles, and preferably a pair of agonist-antagonist muscles, remaining after amputation. The myoelectric signals are picked up by surface electrodes placed on the skin of the amputee adjacent to the muscle remnants. Responsive to the myoelectric signals, the prosthetic limb controller controls the flow of energy from a battery to one or more motors actuating the prosthesis to perform a specified function.

The most advanced prosthetic limbs are able to provide a plurality of degrees of freedom. For instance a prosthetic arm may provide the following three degrees of freedom; (1) wrist pronation and supination, (2) elbow flexion and extension, and (3) hand closing and opening. Each degree of freedom comprises two functions. For instance, the elbow degree of freedom comprising the two functions of (1) flexion and (2) extension. Ideally, a myoelectric prosthetic controller would use the myoelectric signals of the same remnant agonist-antagonist muscle pairs that control normal arms. However, this is only possible for certain below-elbow amputees.

To provide multiple degrees of freedom in a prosthetic limb for above-elbow amputees, or those with shoulder disarticulation, a prosthetic controller must have a means for switching between the various degrees of freedom in addition to means for performing the movements of the specified degree chosen. For instance, in an arm prosthesis for which the user has only biceps and triceps muscle remnants (collectively, a single pair of agonist-antagonist muscles), in one switch state, myoelectric signals of the muscle pair control elbow movements while in another switch state, the signals control hand or wrist movements. Such switching means typically comprises a mechanical switch operated by a predetermined shoulder movement. This switching scheme, however, requires unnatural participation of other body parts.

PCT application No. 008599960 discloses a method and apparatus for multifunction control of a myoelectrically controlled prosthetic limb by recognition of patterns associated with the onset of muscle contraction in a single pair of agonist-antagonist muscles. In the scheme disclosed therein, specific characteristics, such as mean absolute value, slope, zero crossings, wave length, and slope change, of the myoelectric signals associated with the initiation of a plurality of muscle contractions are generated and processed to produce representative primitives or descriptors. The classification of the descriptors can then be accomplished using any number of distance measures as is known in the syntactic pattern recognition art. Alternately, the known descriptors can be used to train a multi-layer neural network using a back propagation algorithom.

The myoelectric patterns and characteristics associated with a single pair of agonist-antagonist muscles are different for each different function. For instance, the biceps-triceps muscle pair would have a particular myoelectric characteristic associated with elbow flexion, but would have a different myoelectric characteristic signal for elbow extension.

The data in the neural network are generated during a training session in which the user performs a plurality of muscle contractions associated with a plurality of functions. Considering an above-elbow amputee having a prosthetic arm, for instance, a single-contact electrode is placed on the biceps remnant and another single-contact, large-contact-surface electrode is placed on the triceps remnant. The differential signal between the electrodes is recorded and the selected characteristics are calculated and averaged.

During normal operation subsequent to training, the controller constantly records and observes a specified interval of the myoelectric signals of the user's muscle pair and determines total energy. If the total energy exceeds a predetermined threshold in a specified interval, pattern recognition software is triggered. The signal in the triggering interval plus the myoelectric signal to follow for another specified interval are placed in a memory and the various characteristics of the stored total interval, such as mean absolute value, etc., are determined and input to the neural network. The prosthesis controller switches to operate the function corresponding to the most closely resembled pattern class and the myoelectric signals from the muscle pair are then used to control that function. The control of the function, once selected, is accomplished by means separate from the selection software and which is not of concern to the present invention.

U.S. Pat. No. 4,030,141 issued to Daniel Graupe discloses a similar scheme for switching among degrees of freedom of a multifunction prosthesis.

These prosthesis control systems are complicated and require significant data processing capacity to perform the complex mathematics needed. The microprocessor and associated circuitry is significant and may not easily fit within the prosthetic device. Further, the electrode arrangement disclosed in PCT application No. 008599960 is prone to receiving faulty signals due to capacitance changes between the two single contact electrodes. In particular, since the electrodes are placed on the opposite side of the limb from each other, muscle contractions commonly will cause the distance between the electrodes, and thus the capacitance, to change leading to interference with the pure myoelectric signals.

Accordingly, it is an object of the present invention to provide an improved prosthetic device.

It is a further object of the present invention to provide an improved prosthesis controller with multiple degrees of freedom.

It is yet a further object of the present invention to provide an improved degree of freedom selection apparatus and method for a prosthesis controller.

It is one more object of the present invention to provide an improved degree of freedom selection apparatus and method for a prosthesis controller which uses commercially available electrodes of proven reliability and signal processing circuitry of proven reliability.

It is yet one more object of the present invention to provide a switching apparatus and method for a myoelectric prosthesis controller having multiple degrees of freedom which recognizes myoelectric signals requiring greatly reduced computational overhead than is known in the prior art.

It is another object of the present invention to provide a myoelectric prosthesis controller of small size and low weight.

It is yet another object of the present invention to provide a switching apparatus and method for a prosthesis controller having multiple degrees of freedom which is highly accurate in recognizing predetermined myoelectric patterns.

SUMMARY OF THE INVENTION

The invention involves a method and apparatus for switching between a plurality of degrees of freedom of a prosthesis. The apparatus includes at least one electrode for picking up myoelectric signals of a muscle (and preferably two electrodes for picking up myoelectric signals of a pair of agonist-antagonist muscles), circuitry for amplifying, full-wave rectifying and smoothing the myoelectric signals, an analog-to-digital converter for converting the received myoelectric signals to digital data, and a microcontroller having memory means and programming to operate the apparatus as disclosed herein.

The apparatus has two modes of operation, a training mode and an operation mode. In the training mode, the electrodes are placed on the selected muscle pair remnants and the user is instructed to perform a particular muscle contraction, preferably a jerk-type contraction, a plurality of times, e.g., 10 times. The two electrodes receive the myoelectric signal corresponding to each of the 10 muscle contractions from the agonist and the antagonist muscles. The data is then amplified, full-wave rectified, smoothed, digitized and stored in memory.

An average pattern is calculated for each of the agonist muscle and the antagonist muscle and stored in a table in memory. As an example, if the interval is selected to be 300 ms and the sampling rate of the analog-to-digital converter is 50 Hz, (a 20 ms period between samples) a total of 15 data points for each of the two channels is generated. Accordingly, in this example, 30 numbers are stored in the reference table.

The microcontroller further calculates which one of the ten sample contractions contains data which deviates the most from the average pattern now stored in the reference table. That deviation is then stored as a 31st data point in the reference table.

In the operating mode, when the user wishes to switch the degree of freedom being controlled, the user performs the predesignated muscle contraction. The apparatus continuously stores, in a circular memory buffer, the myoelectric signal generated in both channels in the last 300 ms (corresponding to the same period and sampling rate used to generate the reference table).

Every time a sample from both muscles comes into the memory buffer, the microcontroller compares the data in the circular memory buffer to the data in the reference table and calculates the deviation between the two. The microcontroller then compares the calculated deviation value with the deviation value stored as the 31st number in the reference table. If the calculated deviation is less than the stored deviation, the microcontroller considers this to be a recognition of the predesignated muscle contraction and instructs the controller to switch degrees of freedom. If the calculated deviation is greater than the deviation stored in the reference table, no action is taken and, when the next sample data point is received from the analog-to-digital converter, another comparison is performed.

In the preferred embodiment, the apparatus is set up to recognize only a single pattern. Accordingly, whenever the user wishes to switch degrees of freedom, he performs the single predesignated muscle contraction and the apparatus is configured to switch degrees of freedom in a predetermined order. If a limb has three degrees of freedom, e.g., (1) elbow movement, (2) wrist movement, and (3) hand movement, the apparatus will switch between these three degrees of freedom in response to the predesignated muscle contraction in a predetermined order. For instance, (1) if the apparatus is currently in the elbow movement mode, a jerk will switch it to the wrist movement mode, (2) if the limb is in the wrist movement mode, a muscle contraction will switch it to the hand movement mode, and (3) if the limb is in the hand movement mode, a muscle contraction will switch it to the elbow movement mode. Accordingly, if the limb is currently in the wrist movement mode and the user wish to switch to the elbow movement mode, he must perform the designated muscle contraction twice.

DETAILED DESCRIPTION OF THE PREFERRED EMBODIMENT

Figure 1:
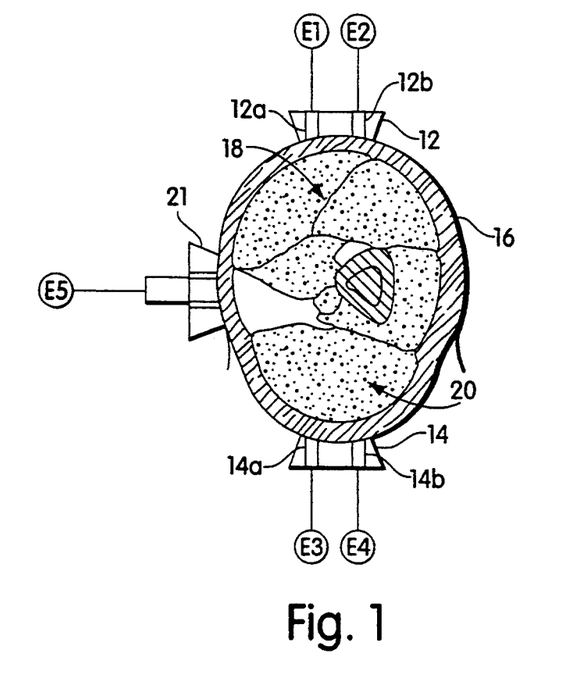
FIG. 1 is a diagram illustrating the placement of electrodes for obtaining myoelectric signals in a preferred embodiment of the invention.

FIG. 1 shows a cross-section of a human upper arm illustrating the type and placement of electrodes for receiving the myoelectric signals of a preferred embodiment of the present invention. The electrodes are of the twin-contact type commonly used with the "Boston elbow". First and second electrodes 12 and 14 are placed on the skin 16 of the user. Electrode 12 is placed adjacent the triceps muscles, generally indicated at 18, while electrode 14 is placed adjacent the biceps muscle, generally indicated at 20. Each electrode comprises two metallic contacts, 12a and 12b, and 14a and 14b, respectively. Accordingly, terminals E1 and E2 provide a differential signal corresponding to the myoelectric signals of the triceps and terminals E3 and E4 provide a differential signal corresponding to the myoelectric signals of the biceps. The use of twin-contact electrodes eliminates the inter-electrode capacitance problem associated with the electrode arrangement suggested in PCT application No. 008599960.

In the particular embodiment discussed herein, the system uses the myoelectric signals of a pair of agonist-antagonist muscles. However, it should be understood that the system can also be designed to use essentially any myoelectric signal. For instance, the apparatus could be adapted to use the myoelectric signals of a single muscle. However, it is believed that the use of a pair of agonist-antagonist muscles results in the most accurate operation of the apparatus.

A third electrode is used as a ground reference and is placed on a part of the body which is not near any muscles. Most commonly, the ground reference electrode would be placed underneath the arm where there are no muscles and hence no myoelectric signals as illustrated in FIG. 1. Only a single ground reference node is needed. Accordingly, a single-contact electrode could be used. Alternately, and as illustrated in FIG. 1, a twin-electrode could be used with the two contacts short-circuited to each other.

Figure 2:
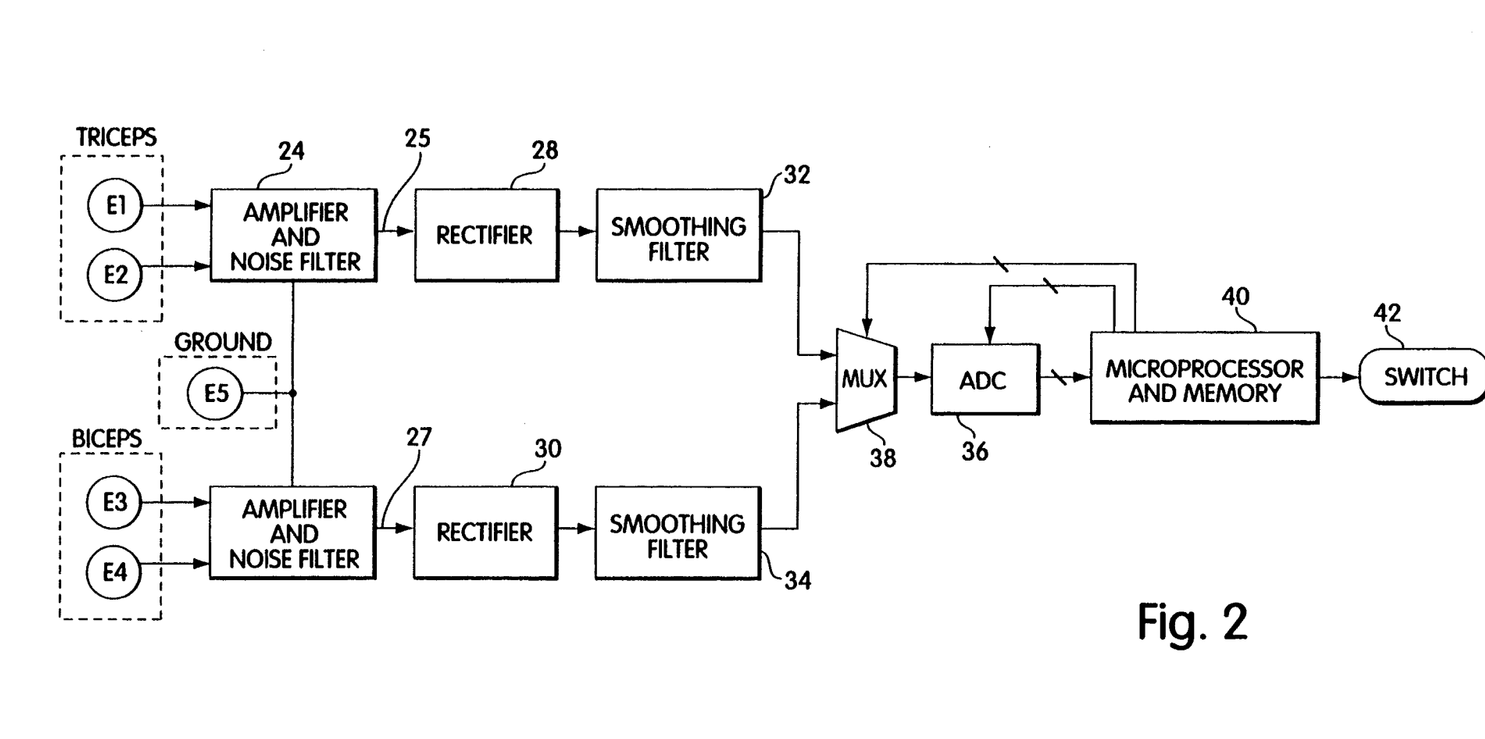
FIG. 2 is a block diagram of a preferred embodiment of the present invention.

FIG. 2 is a block diagram illustrating the various components of the present invention. FIG. 2 and subsequent figures illustrate the circuitry and programming of the present invention for switching between multiple degrees of freedom. It should be understood that a complete myoelectric prosthesis controller comprises additional software and componentry, which are not shown in the figures, for controlling movement of the prosthesis once the degree of freedom has been selected by the circuitry disclosed herein.

Myoelectric signals typically have a magnitude of no more than 10 mV. Accordingly, the myoelectric signals are first amplified by amplifiers 24 and 26 to a more useful level, on the order of a full range of −5 to +5 volts. The electrodes typically pick up a very noisy signal which includes components created by surrounding electrical equipment. Accordingly, blocks 24 and 26 should also include filtering circuitry to eliminate or reduce the electrical noise received by the electrodes. In the "Boston elbow" prosthesis, for example, the amplifying and filtering circuitry is included within the electrode housing itself. The signals on lines 25 and 27 output from blocks 24 and 26 are referred to as the raw myoelectric signals.

The raw myoelectric signals are then full-wave rectified by rectifier circuits 28 and 30 and passed through smoothing filters 32 and 34. In at least one possible embodiment, both the rectification and smoothing may be accomplished by an RMS-to-DC converter. Preferably, however, full-wave rectification and smoothing is accomplished by purpose-built circuitry, such as the circuitry utilized in the "Boston elbow" for full-wave rectification and smoothing.

Myoelectric signals are typically in a frequency range of approximately 40 Hz to 400 Hz. In the preferred embodiment of the present invention, the smoothing filters limit the frequency bandwidth to approximately 10 Hz (0–10 Hz).

The amplified, rectified and smoothed myoelectric signals from each of the two channels (i.e., biceps channel and triceps channel) are converted into digital data by an analog-to-digital converter (ADC) 36 and forwarded to a microprocessor 40. Microprocessor 40 includes RAM memory space for storing the digital representation of the two amplified, rectified and smoothed myoelectric signals.

In at least one possible embodiment, a multiplexer 38 under control of the microprocessor 40 alternately selects the output of filters 32 and 34 to be sent to the input of ADC 36. In this embodiment, microcontroller 40 further controls the destination of the digital data so as to store data from each of the two channels in separate memory sections. Alternately, and depending on size requirements, two ADCs may be used (i.e., one for each channel).

Microprocessor 40 controls switch 42 to switch degrees of freedom responsive to memory myoelectric data meeting predetermined criteria as discussed hereinbelow.

The purpose of the method and apparatus disclosed herein is to switch between degrees of freedom of a prosthesis in response to a predesignated muscle contraction which the user of the limb is trained to perform when he/she wishes to switch between degrees of freedom. For instance, a myoelectrically controlled prosthetic arm may have three degrees of freedom, for instance. The degrees of freedom may comprise; (1) elbow flexion and extension, (2) wrist pronation and supination, and (3) hand closing and opening.

The method and apparatus disclosed herein comprises two modes, a training mode, in which the device as well as the user is trained, and an operation mode, which would be the normal operation mode of the device. Selection of mode may be accomplished by a "one-position-preferred" toggle switch. Such a switch is permanently biased in a first direction, the operation mode, unless the switch is held in the other position, in which case it enters the training mode. The microcontroller would be coupled to receive the information indicative of the state of the switch.

In the training mode, a pattern is generated and stored as a table in memory. The stored table corresponds to a specified muscle contraction in order to switch degrees of freedom of his/her prosthetic limb. In the operation mode, the device continuously compares the incoming myoelectric signals with the stored pattern in order to determine if the user has performed the specified muscle contraction. If the incoming myoelectric signal is sufficiently similar to the data in the stored table, the microprocessor switches degrees of freedom.

In the preferred embodiment, the selected muscle contraction is a fast twitch or jerk-type muscle contraction For instance, in at least one preferred embodiment, the selected pattern is 300 ms of myoelectric signals associated with a fast elbow flexion.

In the training mode, the electrodes are placed on the limb of the user as illustrated in FIG. 1 and previously discussed and the user is asked to perform a fast muscle contraction such as an imagined quick elbow flexion. The microprocessor 40 continuously receives the digitally converted, amplified, rectified and smoothed myoelectric signals. The digital-to-analog converter 36 operates at a frequency to sample each of the signals at least twice their bandwidth in order to satisfy the Nyquist condition. Accordingly, if the smoothed signals are band limited to 10 Hz the ADC must sample each channel at no less than 20 Hz. Since, in the embodiment shown in FIG. 2, a single ADC receives data alternately from each channel, the ADC must operate at a minimum of 40 Hz. In at least one preferred embodiment, the ADC sampled each channel at 50 Hz, i.e., operates at 100 Hz sampling rate.

In the training mode, the microprocessor observes the magnitude of each sample from each channel. For every six samples (three from each channel), it calculates the sum of the six magnitudes and compares that sum with a predetermined, stored threshold value. The microprocessor continues this process until it finds a set of six data points having a sum exceeding the specified threshold, at which point it stores the six sample data points and continues to store the following 12 samples from each channel. (At the exemplary sampling rate of 50 Hz discussed above, i.e., 20 ms intervals, a total of 15 samples per channel is necessary to obtain 300 ms of data). This process is repeated a number of times so as to obtain a plurality of patterns from each channel. In the preferred embodiment, the user is asked to perform approximately 10 of the predesignated muscle contractions and the microprocessor stores the resulting 20 patterns (10 from each channel).

The microprocessor then determines for each channel the average over the 10 patterns of each of the 30 sample points (15 for each channel).

The microprocessor then calculates the deviation of each of the 10 patterns from the calculated average pattern. Each deviation is calculated by simply summing the differences between each of the 30 data points of the stored pattern with the corresponding data points of the average pattern. The largest calculated deviation is then selected and stored along with the average pattern (a total of 31 pieces of data) in a table in memory. The remaining data is discarded.

In the operation mode, the electrodes are again coupled to the user as previously described and the ADC is controlled by the microprocessor to sample each channel at the same frequency as in the training mode, e.g., 50 Hz. The ADC operates continuously and the microprocessor stores the incoming data in a circular memory buffer which always contains the most recent 300 ms of data from each channel. Between each pair of samples (one from each channel) the microprocessor calculates the deviation of the real time data in the circular memory (30 data points) from the data in the stored table and compares the calculated deviation with the maximum deviation stored as the 31st number in the table.

If the calculated deviation exceeds the stored maximum deviation, the microprocessor waits for the next pair of data samples to come in and repeats the process. If and when the calculated deviation is less than or equal to the stored maximum deviation, the microprocessor sends out a signal to the switch controller 42 instructing it to switch from the current degree of freedom to the next degree of freedom. Further, the microprocessor inhibits comparisons for the next 300 ms in order to prevent the device from recognizing a single pattern multiple times. After the 300 ms delay, the device goes back to normal operation and continuously compares the incoming myoelectric signals from the two channels with the stored pattern as just described.

The method and apparatus disclosed herein utilizes greatly simplified mathematics compared to previous systems for switching amongst degrees of freedom of a prosthetic limb. The present invention does not require calculation of various characteristics of the myoelectric signals. Instead, the analog-to-digital converter simply converts the amplified, rectified and smoothed myoelectric signal into a series of data points, each data point comprising the instantaneous amplitude of the respective signal. Accordingly, the present invention requires significantly less processing power. All of the circuitry, including the microprocessor, of the present invention can be enclosed in a light weight package enclosed in a housing approximately $2'' \times 2'' \times \frac{1}{2}''$. The device can be incorporated into a prosthetic limb without inconvenience to the user. Further, in the preferred embodiment, only a single pattern is stored thus reducing the amount of memory space needed and further reducing the necessary processing power.

With only a single pattern stored in memory, the device switches degrees of freedom in some predetermined order. For instance, when the device is operating in the elbow flexion/extension mode and a pattern is recognized, it will switch to the wrist pronation/supination mode. If the device is in the wrist pronation/supination mode and a pattern is recognized, it switches to the hand closing/opening mode. Finally, if the limb is in the hand closing/opening mode, and a pattern is recognized, the device switches to the elbow flexion/extension mode. Accordingly, if the prosthetic arm is currently in the elbow flexion/extension mode, and the user wishes to switch to the hand closing/opening mode, he/she simply must perform the predesignated muscle contraction twice. In a preferred embodiment of the invention, the prosthetic arm also has circuitry or software for returning to the elbow extension/flexion mode from any other mode after a specified period of myoelectric silence in the other modes.

Figure 3:
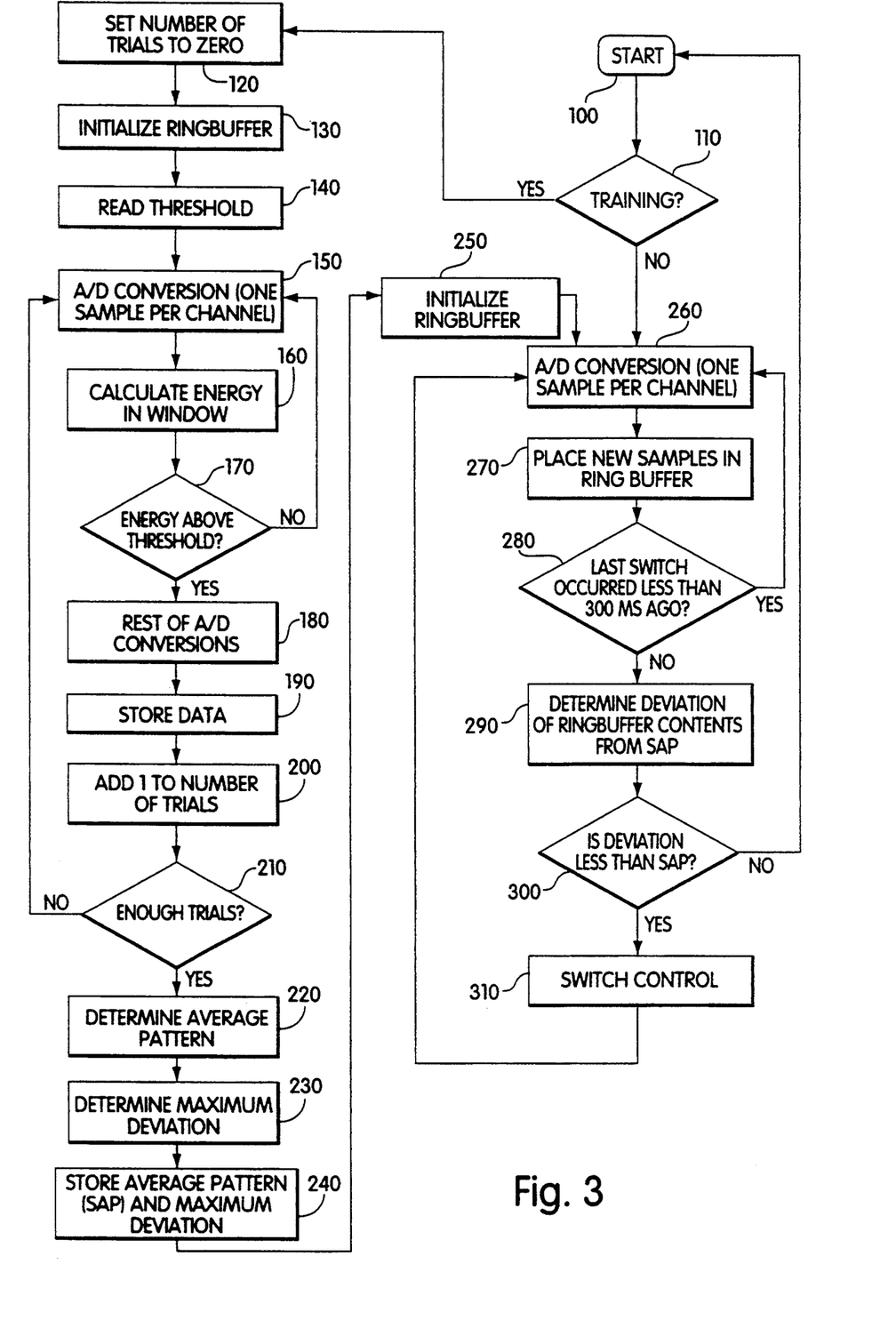
FIG. 3 is a flow chart illustrating the operation of the microcontroller of the present invention.

FIG. 3 is a flow chart illustrating exemplary programming of the microprocessor for achieving the operation described above. Programming starts at step 100. In step 110, the microprocessor first inquires if the training mode has been selected. If training mode is engaged, programming flows to step 120, in which the memory location which is to store the number of trials performed is initialized to 0. In the following step, step 130, the ring buffer (or circular memory) which will store the incoming myoelectric data is also initialized.

In the preferred embodiment, the triggering threshold can be set by the prosthetist or other qualified person. Thus, in step 140, the programming reads the inputted threshold value.

In step 150, the microprocessor accepts and stores one sample from each of the two channels. In step 160, the microprocessor calculates the sum of the six most recent data samples (three from each channel). It should be understood that depending upon the particular application, the triggering energy window may comprise any number of samples per channel and the threshold would be set accordingly.

In step 170, the calculated energy in the specified window is compared with the threshold parameter. If the energy does not exceed that threshold, programming loops back around to step 150. If, however, the energy exceeds the specified threshold, programming proceeds to step 180. In steps 180 and 190, the remaining samples needed to complete the pattern are read by the microprocessor and stored in memory. For instance, if the pattern is 300 ms and the sampling interval is 20 ms, 12 more analog-to-digital conversions per channel are performed and the 30 total pieces of data are stored in memory. In step 200, the number of trials performed is incremented one unit. In step 210, the microprocessor determines if the predetermined number of trials, e.g. 10, have been performed. If not, programming loops back around to step 150. If all 10 trials have been performed, programming proceeds to step 220. In step 220, an average pattern is determined as previously described. In step 230, the maximum deviation is determined as previously described. Finally, in step 240, the average pattern and the calculated maximum deviation are stored in a table in memory.

Flow in the operation mode begins at step 250. In step 250, the ring buffer which stores the last 300 ms of incoming myoelectric data is initialized. In step 260, the microprocessor receives one digital sample of the data from each channel. In step 270, the data is placed in the ring buffer. As previously described, the ring buffer is large enough to store the last 300 ms of data. As previously mentioned, if a pattern detection occurs, the device is inhibited from comparing the incoming data with the stored pattern for 300 ms. Accordingly, in step 280, if the last detection (i.e., switching of degrees of freedom) occurred within the last 300 ms, flow is returned to step 260. If it has been more than 300 ms since the last switching of degrees of freedom of the prosthesis, flow continues to step 290.

In step 290, the microprocessor calculates the deviation of the contents of the ring buffer from the stored average pattern. In step 300, if the deviation calculated in step 290 is more than the stored maximum deviation, programming loops back around to step 100. If the deviation calculated in step 290 exceeds the stored maximum deviation, programming flows to step 310, in which the microprocessor controls the switch controller to switch degrees of freedom. After step 310, programming loops back around to step 260.

Having thus described a few particular embodiments of the invention, various alterations, modifications and improvements will readily occur to those skilled in the art. For instance, the invention can be used to switch between functions instead of or in addition to degrees of freedom. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for switching amongst a plurality of degrees of freedom of a prosthesis comprising the steps of;
    (1) storing a pattern representing myoelectric signals of a muscle corresponding to a predesignated muscle contraction, said pattern comprising a first plurality of data points, each data point being representative of an instantaneous amplitude of said myoelectric signals at an instant in time,
    (2) obtaining a second plurality of data points, each of said second plurality of data points being representative of the instantaneous amplitude of myoelectric signals of said muscle in real time,
    (3) comparing said second set of data points with said first set of data points, and
    (4) switching amongst said degrees of freedom if said real time myoelectric signals are similar to said stored pattern within a predetermined limit.

2. A method as set forth in claim 1 wherein step (1) further comprises the sub-steps of;
    (1.1) causing said predesignated muscle contraction to be performed at least one time,
    (1.2) receiving said myoelectric signals corresponding to said movement,
    (1.3) full wave rectifying said myoelectric signals,
    (1.4) smoothing said myoelectric signals corresponding to said movement,
    (1.5) converting said myoelectric signals corresponding to said movement to digital data, and
    (1.6) storing said digital data in memory as said first plurality of data points.

3. A method as set forth in claim 2 wherein said muscle is a pair of agonist-antagonist muscles.

4. A method as set forth in claim 2 wherein step (1) further comprises the sub-steps of;
    (1.55) repeating steps (1.1) through (1.5) a plurality of times in order to obtain a plurality of patterns, and
    (1.56) determining an average pattern based on said plurality of patterns generated, said first plurality of data points comprising said average pattern.

5. A method as set forth in claim 4 wherein step (2) further comprises the sub-steps of;
    (2.1) receiving said real time myoelectric signals,
    (2.2) smoothing said real time myoelectric signals, and
    (2.3) converting said real time myoelectric signals to digital data.

6. A method as set forth in claim 5 wherein step (1) further comprises the sub-steps of;
    (1.8) determining the deviation of each of said plurality of patterns from said average pattern,
    (1.9) determining said pattern having a maximum deviation from said average pattern, and
    (1.10) storing said maximum deviation.

7. A method as set forth in claim 6 wherein step (3) comprises;
    (3.1) determining the deviation of said second plurality of data points from said first plurality of data points.

8. A method as set forth in claim 7 wherein step (4) comprises;
    (4.1) switching degrees of freedom only if said deviation of said second plurality of data points from said first plurality of data points is less than or equal to said stored maximum deviation.

9. A method as set forth in claim 8 wherein said prosthesis has at least first and second degrees of freedom, said prosthesis at any given time being in a first mode in which it controls said first degree of freedom or in a second mode in which it controls said second degree of freedom and wherein step (4.1) further comprises the step of;
    (4.1.1) if said prosthesis is in said first mode, switching to said second mode, and if said prosthesis is in said second mode, switching to said first mode.

10. A method as set forth in claim 9 further comprising the step of;
    (1.2.1) amplifying said myoelectric signal.

11. A method as set forth in claim 10 further comprising the step of (1.2.05) filtering noise out of said myoelectric signal.

12. A method as set forth in claim 11 wherein said predesignated muscle contraction is a fast muscle contraction.

13. A method as set forth in claim 12 wherein said stored pattern comprises approximately 300 milliseconds of data and wherein steps (1.4) and (2.2) comprise smoothing so as to eliminate frequency components above approximately 10 Hz and steps (1.5) and (2.3) comprise converting at a rate of 50 Hz.

14. A method as set forth in claim 13 wherein said plurality of times referred to in step (1.6) comprises approximately 10 times.

15. An apparatus for switching amongst a plurality of degrees of freedom of a prosthesis comprising;
    memory means for storing a a first plurality of data points corresponding to myoelectric signals generated by a muscle corresponding to a predesignated muscle contraction, each data point being representative of an instantaneous amplitude of said myoelectric signals corresponding to said predesignated muscle contraction, means for receiving myoelectric signals from said muscle, means for converting said myoelectric signals to a second plurality of data points, each data point being representative of an instantaneous amplitude of said received myoelectric signal, processing means for comparing said second plurality of data points with said first plurality of data points, and means for switching degrees of freedom of said prosthesis responsive to said second plurality of data points being similar to said first plurality of data points within a specified tolerance.

16. An apparatus as set forth in claim 15 wherein said first plurality of data points comprises myoelectric signals generated by first and second muscles, respectively, of a pair of agonist-antagonist muscles, and wherein said means for receiving myoelectric signals comprises first means for receiving first myoelectric signals from said first muscle and second means for receiving second myoelectric signals from said second muscle.

17. An apparatus as set forth in claim 16 wherein;
said converting means converts said myoelectric signals to digital data at a specified rate corresponding to the data of said first plurality of data points, and said processing means comprises;
   means for continuously storing, as said second plurality of data points, data points corresponding to a specified interval of the immediately preceding first and second myoelectric signals, and
   means for comparing said data points of said stored specified interval of said immediately preceding first and second myoelectric signals with said first plurality of data points each time a pair of data points is converted.

18. An apparatus as set forth in claim 17 wherein said means for receiving said first myoelectric signals and said means for receiving said second myoelectric signals each comprise;
   a twin-contact electrode placed on a skin surface adjacent to the respective muscle,
   an amplifier for amplifying said myoelectric signals,
   a filter for removing noise from said myoelectric signals,
   a full-wave rectifier,
   a smoothing circuit for smoothing said myoelectric signal, and
   wherein said means for converting comprises an analog-to-digital converter.

19. An apparatus as set forth in claim 18 wherein,
said processing means further comprises means for determining the deviation of said second plurality of data points from said first plurality of data points, and
said means for switching is responsive to said deviation for switching degrees of freedom when said deviation is less than a specified value.

20. An apparatus as set forth in claim 19 wherein said prosthesis has at least first and second degrees of freedom, said prosthesis at any given time being in a first mode in which it controls said first degree of freedom or in a second mode in which it controls said second degree of freedom and wherein said switching means comprises;

means for switching said prosthesis to said second mode, if said prosthesis is in said first mode, and means for switching said prosthesis to said first mode, if said prosthesis is in said second mode.

21. An apparatus as set forth in claim 20 wherein said predesignated muscle contraction is a fast muscle contraction.

22. An apparatus as set forth in claim 21 wherein said first plurality of data points and said second plurality of data points each comprise approximately 300 milliseconds of digital data sampled at a rate of approximately 50 Hz.

23. An apparatus as set forth in claim 22 further comprising means for obtaining said first plurality of data points, said means comprising;
   means for obtaining a plurality of patterns of said myoelectric signals from said first and second muscles corresponding to a plurality of said predesignated muscle contractions,
   means for determining said first plurality of data points by determining the average value for each data point of said plurality of patterns,
   means for determining the deviation of each of said plurality of patterns from said average values,
   means for determining which one of said plurality of patterns has a maximum deviation from said average pattern, and
   means for storing said average pattern at said first set of data points and said maximum deviation, said maximum deviation comprising said specified threshold.

24. An apparatus for switching amongst a plurality of degrees of freedom of a prosthesis comprising;
   a digital memory for storing a first plurality of data points corresponding to first and second myoelectric signals generated by first and second muscles, respectively, of a pair of agonist-antagonist muscles corresponding to a predesignated muscle contraction, each data point being representative of an instantaneous amplitude of said myoelectric signals at an instant in time,
   a first electrode for receiving first myoelectric signals from said first electrode,
   a second electrode for receiving second myoelectric signals from said second muscle,
   a rectifier for full-wave rectifying said first and second myoelectric signals,
   a smoothing circuit for smoothing said first and second myoelectric signals,
   an analog-to-digital converter for converting said first and second myoelectric signals to a second plurality of data points, each of said second plurality of data points being representative of an instantaneous amplitude of said first or second myoelectric signals, respectively,
   processing means for comparing said second plurality of data points with said first plurality of data points, and
   a switch for switching degrees of freedom of said prosthesis responsive to said second plurality of data points being similar to said first plurality of data points within a specified tolerance.

25. An apparatus for switching amongst a plurality of degrees of freedom of a prosthesis comprising;
   a digital memory for storing a first set of data points corresponding to first and second myoelectric signals generated by first and second muscles, respectively, of a pair of agonist-antagonist muscles corresponding to a predesignated muscle contraction, each data point being representative of an instantaneous amplitude of said myoelectric signals at an instant in time, a first twin-contact electrode for receiving first myoelectric signals from said first muscle, a second twin-contact electrode for receiving second myoelectric signals from said second muscle, a third electrode for receiving a ground reference signal, an amplifier for amplifying said first and second myoelectric signals, a filter for removing noise from said first and second myoelectric signals, a rectifier for full-wave rectifying said first and second myoelectric signals, a smoothing circuit for smoothing said first and second myoelectric signals, an analog to digital converter for converting said first and second myoelectric signals to a second plurality of data points, each of said second plurality of data points being representative of an instantaneous amplitude of said first or second myoelectric signals, at a specified rate corresponding to the data on said first set of data points, processing means comprising, means for continuously storing, as said second plurality of data points, data points corresponding to a specified interval of the immediately preceding first and second myoelectric signals, means for comparing said second plurality of data points with said first plurality of data points every time a pair of data points is converted, and means for determining the deviation of said second plurality of data points from said first plurality of data points, and means for switching degrees of freedom of said prosthesis responsive to said deviation being less than a specified value.

26. A method as set forth in claim 3 wherein said muscle is a pair of agonist-antagonist muscles.

* * * * *